US012700095B2

(12) United States Patent
Oh et al.

(10) Patent No.: US 12,700,095 B2
(45) Date of Patent: Aug. 4, 2026

(54) METHOD FOR PREDICTING STATE OF OBJECT ON BASIS OF DYNAMIC IMAGE DATA AND COMPUTING DEVICE PERFORMING SAME

(71) Applicants: THE ASAN FOUNDATION, Seoul (KR); UNIVERSITY OF ULSAN FOUNDATION FOR INDUSTRY COOPERATION, Ulsan (KR)

(72) Inventors: Jungsu Oh, Seoul (KR); Jae Seung Kim, Seoul (KR); Minyoung Oh, Seoul (KR); Dong Yun Lee, Seoul (KR); Seung Jun Oh, Seoul (KR); Sang Ju Lee, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 259 days.

(21) Appl. No.: 18/667,146

(22) Filed: May 17, 2024

(65) Prior Publication Data

US 2024/0303815 A1 Sep. 12, 2024

Related U.S. Application Data

(63) Continuation of application No. PCT/KR2022/018157, filed on Nov. 17, 2022.

(30) Foreign Application Priority Data

Nov. 18, 2021 (KR) ........................ 10-2021-0159760

(51) Int. Cl.
*G06T 7/00* (2017.01)
*A61B 6/03* (2006.01)
(Continued)

(52) U.S. Cl.
CPC ............ *G06T 7/0012* (2013.01); *A61B 6/037* (2013.01); *A61B 6/507* (2013.01);
(Continued)

(58) Field of Classification Search
CPC ......... G06T 7/0012; G06T 2207/10016; G06T 2207/10104; G06T 2207/20081;
(Continued)

(56) References Cited

U.S. PATENT DOCUMENTS 8,831,323 B2 * 9/2014 Kelly ........................ G06T 7/20
382/131
10,765,382 B2 9/2020 Liu et al.
(Continued)

FOREIGN PATENT DOCUMENTS

CN 106887025 A 6/2017
KR 10-2015-0009915 A 1/2015
(Continued)

OTHER PUBLICATIONS

International Search Report issued Feb. 21, 2023 in PCT/KR2022/018157 filed on Nov. 17, 2022, 2 pages.
(Continued)

*Primary Examiner* — Michael S Osinski
(74) *Attorney, Agent, or Firm* — Oblon, McClelland, Maier & Neustadt, L.L.P.

(57) ABSTRACT

The present invention relates to a method for predicting a state of an object on the basis of dynamic image data and a computing device performing same, the method enabling initial dynamic image data and delay image data to be predicted by performing learning on the basis of dynamic image data captured at a time point when both blood flow image information and disease-specific biological information are included, and furthermore, enabling blood flow
(Continued)

image information and disease-specific biological information of the object to be provided.

15 Claims, 11 Drawing Sheets

(51) Int. Cl.
| | | |
|---|---|---|
| *A61B 6/50* | (2024.01) | |
| *A61K 51/04* | (2006.01) | |
| *G06V 10/774* | (2022.01) | |

(52) U.S. Cl.
CPC ........ *A61K 51/0491* (2013.01); *G06V 10/774* (2022.01); *G06T 2207/10016* (2013.01); *G06T 2207/10104* (2013.01); *G06T 2207/20081* (2013.01); *G06T 2207/20084* (2013.01); *G06T 2207/30104* (2013.01); *G06V 2201/03* (2022.01)

(58) Field of Classification Search
CPC . G06T 2207/20084; G06T 2207/30104; G06T 7/0016; G06T 7/11; G06T 2207/10116; G06T 7/20; G06T 2207/10081; G06T 2207/10088; G06T 2207/30101; A61B 6/037; A61B 6/507; A61B 6/00; A61B 6/03; A61B 6/5217; A61B 6/501; A61B 6/504; A61B 5/026; A61K 51/0491; G06V 10/774; G06V 2201/03; G16H 50/50; G16H 50/70; G16H 30/40; G16H 30/20; G16H 50/20; G16H 50/30
See application file for complete search history.

(56) References Cited

U.S. PATENT DOCUMENTS

| | | | | |
|---|---|---|---|---|
| 11,069,064 B2 * | 7/2021 | Sørensen | ............... | A61B 6/481 |
| 11,449,210 B2 * | 9/2022 | Bae | .......................... | G06F 3/038 |
| 11,694,339 B2 * | 7/2023 | Schormans | .......... | A61B 6/5217 |
| | | | | 600/431 |
| 12,056,890 B2 * | 8/2024 | Shin | ..................... | A61B 5/7267 |
| 12,059,237 B2 * | 8/2024 | Sahbaee Bagherzadeh | ................ | |
| | | | | A61B 5/026 |
| 12,106,856 B2 * | 10/2024 | Keshwani | ............. | G06N 3/045 |

| | | | | |
|---|---|---|---|---|
| 12,308,107 B2 * | 5/2025 | Yi | ........................... | G16H 30/40 |
| 12,431,243 B2 * | 9/2025 | Ahmad | ................ | G16H 50/20 |
| 2006/0239585 A1 * | 10/2006 | Valadez | .................... | G06T 5/50 |
| | | | | 382/275 |
| 2013/0116557 A1 * | 5/2013 | Yoshikawa | .............. | A61B 8/06 |
| | | | | 600/431 |
| 2015/0023574 A1 | 1/2015 | Sohn et al. | | |
| 2015/0310598 A1 * | 10/2015 | Rooney | ..................... | G06T 7/00 |
| | | | | 382/131 |
| 2016/0051200 A1 * | 2/2016 | Chino | .................. | A61B 5/0033 |
| | | | | 600/431 |
| 2017/0245766 A1 * | 8/2017 | Flower | ................. | A61B 5/6826 |
| 2018/0133350 A1 * | 5/2018 | Zanzonico | ......... | A61K 51/1057 |
| 2018/0204326 A1 * | 7/2018 | Noji | .................... | A61B 6/5217 |
| 2019/0008468 A1 | 1/2019 | Liu et al. | | |
| 2019/0150763 A1 * | 5/2019 | Gladshtein | ........... | A61B 3/1241 |
| 2019/0159683 A1 * | 5/2019 | Ma | ......................... | G16H 30/40 |
| 2019/0357874 A1 * | 11/2019 | Yoshiara | .................. | A61B 8/06 |
| 2020/0034964 A1 * | 1/2020 | Shimamura | ............... | G06T 7/20 |
| 2020/0178794 A1 * | 6/2020 | El-Baz | ................. | A61B 3/1241 |
| 2020/0288965 A1 * | 9/2020 | Gamliel | ..................... | G06T 5/94 |
| 2020/0355694 A1 * | 11/2020 | Aimiya | ............. | A61K 49/0008 |
| 2021/0264613 A1 * | 8/2021 | Wang | ................... | G06V 10/774 |
| 2022/0117508 A1 * | 4/2022 | Dharmakumar | ......... | A61B 5/00 |
| 2023/0147968 A1 * | 5/2023 | Knobloch | ............... | G06T 11/00 |
| | | | | 382/131 |
| 2023/0153995 A1 * | 5/2023 | Taneda | .................. | G06T 7/0012 |
| | | | | 382/132 |
| 2023/0218223 A1 * | 7/2023 | Knobloch | ............ | A61B 5/4244 |
| | | | | 382/128 |
| 2024/0193781 A1 * | 6/2024 | Otani | .................... | G06T 7/0016 |
| 2024/0420331 A1 * | 12/2024 | Kim | ....................... | A61B 6/507 |

FOREIGN PATENT DOCUMENTS

| | | | |
|---|---|---|---|
| KR | 10-2018-0040287 A | 4/2018 | |
| KR | 10-2019-0127247 A | 11/2019 | |
| KR | 10-2020-0055425 A | 5/2020 | |
| KR | 10-2020-0102416 A | 8/2020 | |

OTHER PUBLICATIONS

Korean Office Action issued Sep. 7, 2023 in Korean Application No. 10-2021-0159760 filed on Nov. 18, 2021, 7 pages (with partial English Translation).

* cited by examiner

Early dynamic image
data

Delay image
data

Radiation dose
of target area

Time Activity Curve of F-18 FP-CIT PET

V711

V712

V713

V714

D711

V715

METHOD FOR PREDICTING STATE OF OBJECT ON BASIS OF DYNAMIC IMAGE DATA AND COMPUTING DEVICE PERFORMING SAME

CROSS-REFERENCE TO RELATED APPLICATIONS

The present application is a continuation of International Patent Application No. PCT/KR2022/018157, filed on Nov. 17, 2022, which is based upon and claims the benefit of priority to Korean Patent Application No. 10-2021-0159760 filed on Nov. 18, 2021. The disclosures of the above-listed applications are hereby incorporated by reference herein in their entirety.

BACKGROUND

Embodiments of the present disclosure described herein relate to a method for predicting a state of an object based on dynamic image data and a computing device for performing the same, and more particularly, relate to a method and an apparatus for predicting an image for diagnosis, which is used when diagnosing a patient based on dynamic image data, and predicting the state of the object.

A positron emission computed tomography (PET) examination is a cutting-edge nuclear medicine imaging method for administering a positron-emitting radioisotope and obtaining radiation emitted outside the human body to obtain pieces of useful diagnostic information associated with metabolic changes and receptor distribution in the human body. Recently, going one step further from obtaining only simple PET images, it is evolving into a hybrid scanner which is fused with computed tomography (CT) or magnetic resonance image (MRI) equipment. Thus, in the current PET examination, as a PET/CT scanner which combines a PET device and a CT device in one body is used by default, anatomical information from the CT image may be additional obtained and accurate position and depth information of the lesion identified from the PET image may be provided.

In general, the PET examination is performed by injecting a tracer labeled with a radioactive isotope into the human body and then performing the diagnosis of a patient based on PET images obtained after lapse of a specific time (e.g., 2 to 3 hours) when the specific and non-specific binding of the tracer reaches a stable state or the difference is maximized.

In other words, to obtain a PET image in which the influence of blood flow is excluded (e.g., when using [18F] FP-CIT or [18F] Florbetaben/Flutemetamol/Florbetapir as a tracer) or obtain a PET image with a large ratio difference between areas (e.g., when using [18F] FDG as a tracer), PET images are obtained after the specific time elapses. In detail, among nuclear medicine imaging, radiopharmaceuticals (radiotracer or radioligand) used in many clinically used tests have different drug dynamics in the body, but in most cases, imaging starts more than 1 hour after injection to obtain delay image data.

SUMMARY

Embodiments of the present disclosure provide a method for predicting a state of an object based on dynamic image data to perform learning based on dynamic image data captured at a time point when both of blood flow image information and disease-specific information are included to predict early dynamic image data and delay image data and additionally provide anatomical information and disease-specific biological information of a corresponding object and a computing device for performing the same.

The technical problems to be solved by the present disclosure are not limited to the aforementioned problems, and any other technical problems not mentioned herein will be clearly understood from the following description by those skilled in the art to which the present disclosure pertains.

According to an embodiment, a method for predicting a state of an object based on dynamic image data may include obtaining a plurality of pieces of image data for training, extracting a plurality of pieces of dynamic image data for training from the plurality of pieces of image data for training, the plurality of pieces of dynamic image data for training including a playback interval image from a first time when a blood flow influence starts to decrease to a predetermined reference time point, after a time point when a drug is injected into a learning object included in each of the plurality of pieces of image data for training, obtaining blood flow image information and disease-specific information corresponding to the plurality of pieces of dynamic image data for training, performing learning using a first image prediction model for diagnosis to generate first training data, based on the blood flow image information and the disease-specific information corresponding to the plurality of pieces of dynamic image data for training, and predicting the blood flow image information and the disease-specific information corresponding to a diagnosis object using dynamic image data for diagnosis and the first training data, when the dynamic image data for diagnosis corresponding to the diagnosis object is obtained.

At this time, the method may further include obtaining early dynamic image data including a playback interval image from the time point when the drug is injected to the first time, the early dynamic image data corresponding to the dynamic image data for training, and delay image data including a playback interval image after the reference time point. The obtaining of the blood flow image information and the disease-specific information corresponding to the plurality of pieces of dynamic image data for training may include obtaining the blood flow image information based on the early dynamic image data and obtaining the disease-specific information based on the delay image data.

At this time, the predicting of the blood flow image information and the disease-specific information corresponding to the diagnosis object may include predicting new early dynamic image data and new delay image data corresponding to the dynamic image data for diagnosis based on the dynamic image data for diagnosis and the first training data.

At this time, the predicting of the blood flow image information and the disease-specific information corresponding to the dynamic image data for diagnosis may include normalizing the image data for training and image data for diagnosis based on a maximum value or an average value between brightness of the dynamic image data for training and brightness of the dynamic image data for diagnosis and predicting the new early dynamic image data and the new delay image data corresponding to the image data for diagnosis.

Furthermore, the forming of the first training data may include matching and learning a change in each pixel in the dynamic image data for training over time with each pixel in the early dynamic image data and the delay image data.

At this time, the image data for training may be positron emission tomography image data.

Furthermore, when the drug used to capture the image data for training is a tracer bound to a specific target area, the dynamic image data for training may be formed as image data obtained continuously or discontinuously from a time point when a dose ratio difference value between the target area and a reference area is greater than or equal to a specific value or an amount of change in dose in the reference area due to blood flow decreases to a time point when the dose ratio difference value is maximized.

At this time, the predetermined reference time point may be determined based on a type of the tracer.

Meanwhile, the method may further include predicting early dynamic image data and delay image data using the dynamic image data by means of a second image prediction model for diagnosis and using the predicted early dynamic image data and the predicted delay image data together to form second training data for predicting the blood flow image information and the disease-specific information.

Furthermore, the method may further include predicting the blood flow image information and the disease-specific information, using an image prediction model for diagnosis, the image prediction model having higher accuracy between accuracy of the first image prediction model for diagnosis and accuracy of the second image prediction model for diagnosis, the first image prediction model for diagnosis and the second image prediction model for diagnosis corresponding to the image data.

According to an embodiment, a computing device for performing a method for predicting a state of an object based on dynamic image data may include a display, a memory storing an image prediction model for diagnosis, and at least one processor that communicates with the display and the memory. The at least one processor may obtain a plurality of pieces of image data for training, may extract a plurality of pieces of dynamic image data for training from the plurality of pieces of image data for training, the plurality of pieces of dynamic image data for training including a playback interval image from a first time when a blood flow influence starts to decrease to a predetermined reference time point, after a time point when a drug is injected into a learning object included in each of the plurality of pieces of image data for training, may obtain blood flow image information and disease-specific information corresponding to the plurality of pieces of dynamic image data for training, may perform learning using a first image prediction model for diagnosis to generate first training data, based on the blood flow image information and the disease-specific information corresponding to the plurality of pieces of dynamic image data for training, and may predict the blood flow image information and the disease-specific information corresponding to a diagnosis object using dynamic image data for diagnosis and the first training data, when the dynamic image data for diagnosis corresponding to the diagnosis object is obtained.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
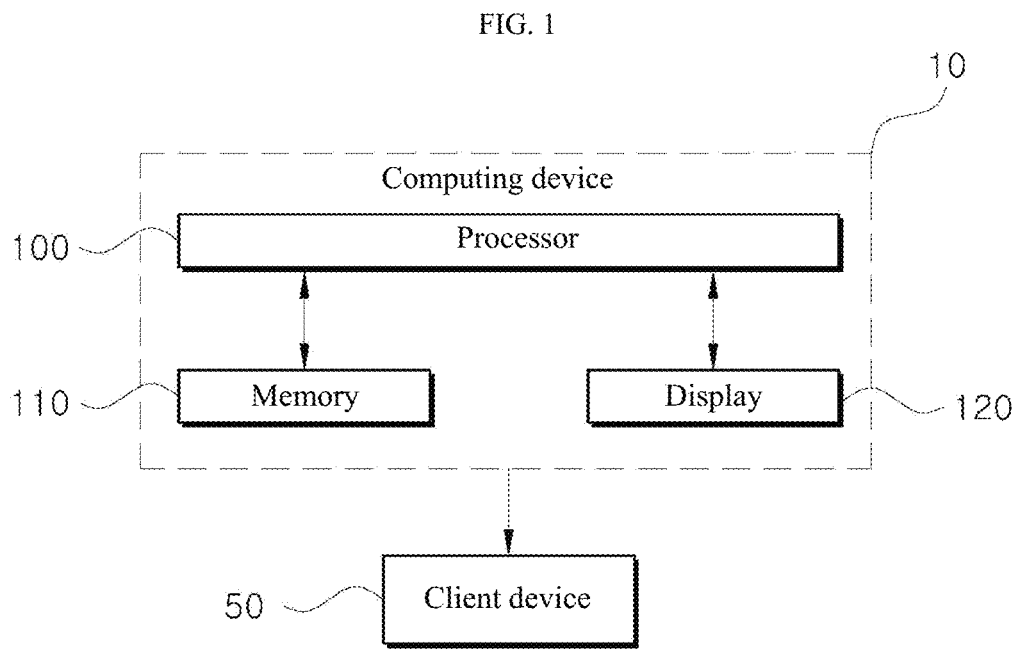
FIG. 1 is a drawing illustrating a control block diagram of a computing device for predicting a state of an object according to an embodiment of the present disclosure.

Hereinafter, an embodiment of the present disclosure will be described in detail with reference to the accompanying drawings. Advantages, features, and methods of accomplishing the same in the present disclosure will become apparent with reference to embodiments described in detail below together with the accompanying drawings. However, the present disclosure is not limited to the embodiments disclosed below, but may be implemented in various forms. The embodiments of the present disclosure are provided to make the disclosure of the present disclosure complete and fully inform those skilled in the art to which the present disclosure pertains of the scope of the present disclosure. The same reference denotations refer to the same components throughout the specification.

Unless otherwise defined herein, all terms (including technical and scientific terms) used in the specification may have the same meaning that is generally understood by a person skilled in the art. Also, terms which are defined in a dictionary and commonly used should be interpreted as not in an idealized or overly formal detect unless expressly so defined.

The terms used herein are provided to describe embodiments, not intended to limit the present disclosure. In the specification, the singular forms include plural forms unless particularly mentioned. The expressions "comprise" and/or "comprising" used herein indicate existence of one or more other elements other than stated elements but do not exclude presence of additional elements.

The "computing device" in the specification may include all of various devices which perform operation processing. The "computing device" may include one or more computers. For example, the computer may correspond to a smartphone, a tablet personal computer (PC), a cellular phone, a personal communication service (PCS) phone, a synchronous/asynchronous international mobile telecommunication-2000 (IMT-2000) mobile phone, a palm PC, a personal digital assistant (PDA), or the like as well as a desktop PC or a note book. Furthermore, the computer may correspond to medical equipment which obtains or observes a medical image. Furthermore, the computer may correspond to a server computer connected with various client computers.

The "image data" in the specification may refer to an image obtained by a medical imaging device.

The "medical imaging device" in the specification refers to a device used to obtain a medical image. For example, the "medical imaging device" may include a positron emission tomography imaging device, a magnetic resonance imaging (MRI) device, or the like.

The "delay image data" in the specification is obtained after a reference time, which refers to an image for diagnosis, which is used to diagnose a patient.

The "reference time" in the specification refers to a time from an initial time point when a drug (e.g., a contrast agent or a tracer) is injected to a time point (i.e., a reference time point) when it is able to obtain image data capable of diagnosing a state of a patient.

The "drug" in the specification refers to being injected into the body when medical image data is captured. For example, the "drug" may correspond to a contrast agent used for magnetic resonance imaging (MRI) or computed tomography (CT), a tracer used to upon positron emission tomography imaging, or the like.

The "early dynamic image data" in the specification refers to image data including a plurality of consecutive image frames. The "early dynamic image data" is obtained before the reference time point when the delay image data is obtained, which is obtained in an early time range (e.g., a time range after a short time after inserting a contrast agent or a tracer administered upon imaging).

The dynamic image data in the specification may refer to image data in which the early dynamic image data and the delay image data are excluded from image data.

In detail, the dynamic image data may refer to a playback interval image from a first time when a blood flow influence starts to decrease to a predetermined reference time point, after a time point when a drug is injected into a learning object included in each of a plurality of pieces of image data, and the playback interval image may include true-early interval.

The blood flow image information in the specification may refer to image data indicated by flow of blood flow of the object.

The disease-specific information in the specification may refer to image data usable to determine a state of the object as the drug remains at a specific residual position.

The "early dynamic image data for training" in the specification refers to early dynamic image data included in training data used to train an image prediction model for diagnosis.

The "delay image data for training" in the specification refers to delay image data included in training data used to train an image prediction model for diagnosis.

The "dynamic image data for training" in the specification refers to dynamic image data included in training data used to train an image prediction model for diagnosis.

The "dynamic image data for diagnosis" in the specification refers to dynamic image data obtained to calculate blood flow image information and disease-specific information of a specific patient.

The "new delay image data" in the specification refers to delay image data calculated by means of an image prediction model for diagnosis to diagnose the specific patient.

The "new early delay image data" in the specification refers to early dynamic image data calculated by means of the image prediction model for diagnosis to diagnose the specific patient.

The "first time" in the specification refers to a time range in which early dynamic image data is obtained. In other words, the "first time" refers to a time range from a time point when early dynamic image data starts to be obtained to a time point when a last image frame is obtained.

The "early time range" in the specification refers to a time range for extracting the first time to obtain early dynamic image data for training.

The "early dynamic image data for initial setting" in the specification refers to image data including a plurality of image frames which are consecutive in the early time range.

The "delay image data for early setting" in the specification refers to delay image data used to calculate the first time suitable for training the image prediction model for diagnosis. The "delay image data for early setting" may be the same as delay image data for training.

Hereinafter, a description will be given in detail of a method and a program for generating an image for diagnosis based on early dynamic image data according to embodiments of the present disclosure with reference to the accompanying drawings.

FIG. 1 is a drawing illustrating a control block diagram of a computing device for predicting a state of an object according to an embodiment of the present disclosure.

Referring to FIG. 1, a computing device 10 according to an embodiment of the present disclosure may include a memory 110, a processor 100, and a display 120.

The memory 110 may store various pieces of data including an image prediction model for diagnosis.

The memory 110 may be implemented as, but not limited to, at least one of non-volatile memory elements, such as a cache, a read only memory (ROM), a programmable ROM (PROM), an erasable programmable ROM (EPROM), an electrically erasable programmable ROM (EEPROM), and a flash memory, a volatile memory element, such as a random access memory (RAM), or storage media, such as a hard disk drive (HDD) and a CD-ROM. The memory 110 may be a memory implemented as a chip independent of the processor 100 which will be described below and may be implemented with the processor 100 as a single chip.

The display 120 may output the above-mentioned various image data.

The display 120 may be provided with a cathode ray tube (CRT), a digital light processing (DLP) panel, a plasma display penal, a liquid crystal display (LCD) panel, an electro luminescence (EL) panel, an electrophoretic display (EPD) panel, an electrochromic display (ECD) panel, a light emitting diode (LED) panel, an organic light emitting diode (OLED) panel, or the like, but not limited thereto.

The processor 100 may obtain image data for training from a client device 50. The client device 50 may be provided as the above-mentioned medical imaging device.

The processor 100 may extract a plurality of pieces of dynamic image data for training from a plurality of pieces of image data (dynamic-framed multiple image data (e.g., either frame-mode or list-mode)) for training.

The processor 100 may obtain blood flow image information and disease-specific information corresponding to the plurality of pieces of dynamic image data for training.

Meanwhile, the processor 100 may perform learning using a first image prediction model for diagnosis, based on the blood flow image information and the disease-specific information corresponding to the plurality of pieces of dynamic image data for training, to generate first training data.

In detail, the processor 100 may map the blood flow image information and the disease-specific information to dynamic image data and may perform learning by means of the first image prediction model for diagnosis based on it to generate the first training data capable of being used for future diagnosis.

When dynamic image data for diagnosis corresponding to a diagnosis object is obtained, the processor 100 may predict blood flow image information and disease-specific information corresponding to the diagnosis object using the dynamic image data for diagnosis and the first training data.

In other words, the processor 100 may predict the blood flow image information and the disease-specific information corresponding to the object using only the dynamic image data and the first training data even without delay image data or early dynamic image data of the object.

The computing device 10 may obtain dynamic image data for training from the client device 50 to construct training data.

For example, when dynamic image data is obtained from a specific patient, the computing device 10 may receive the dynamic image data for the specific patient from the medical imaging device or the client device 50 connected with the medical imaging device.

Meanwhile, image quality of a dynamic image frame of the dynamic image data may be set according to the number of frames. In other words, when the same amount of drug is used, because the maximum amount of radiation emitted to the outside is limited and the amount of signal used to generate an image frame is limited, the computing device 10 may differently set image quality of each image frame depending on the number of image frames based on the same amount of signal.

For example, when the number of image frames increases, because a time length used to generate each image frame become short and the amount of signal available to generate one image frame decreases, the computing device 10 may generate image quality of each image frame to be low.

As an embodiment, the computing device 10 may match and learn a change in each pixel in dynamic image data over time with each pixel in early image data and delay image data.

In other words, in an image data combination for the specific patient (i.e., a combination of early dynamic image data, dynamic image data, and delay image data), the computing device 10 may predict early dynamic image data and delay image data from dynamic image data for each point (i.e., pixel) of body tissue (e.g., brain tissue), may match blood flow image information in the early dynamic image data with disease-specific information in the delay image data to construct a dataset for each image data combination, and may learn a dataset for a plurality of patients for each point (i.e., pixel) to construct an image prediction model for diagnosis.

As an embodiment, the image prediction model for diagnosis may be constructed as a deep neural network (DNN). In other words, the image prediction model for diagnosis may apply a deep learning algorithm to learn dynamic image data for one or more patients.

The DNN refers to a system or a network, which constructs one or more layers in one or more computers and performs determination based on a plurality of pieces of data. For example, the DNN may be implemented with a set of layers including a convolutional pooling layer, a locally-connected layer, and a fully-connected layer. The convolutional pooling layer or the locally-connected layer may be configured to extract features in an image. The fully-connected layer may determine a correlation between the features of the image. In some embodiments, the entire structure of the DNN may be implemented in a form where the locally-connected layer is connected with the convolutional pooling layer and the fully-connected layer is connected with the locally-connected layer. The DNN may include various determination criteria (i.e., parameters) and may add a new determination criterion (i.e., a parameter) by analyzing the input image.

As an embodiment, the DNN may be a structure called a convolutional neural network suitable for image analysis, which may be configured in a structure in which a feature extraction layer for learning a feature with the largest discriminative power by itself from pieces of given image data and a prediction layer for training a prediction model to have the highest prediction performance based on the extracted feature are integrated with each other.

The feature extraction layer may be formed in a structure where a convolution layer for applying a plurality of filters to each area of an image to generate a feature map and a pooling layer capable of spatially integrating the feature map to extract a characteristic which is invariant to a change in position or rotation are alternately repeated several times. As a result, various levels of characteristics from a low level of characteristics, such as a point, a line, or a surface, to a high level of characteristics which are complicated and meaningful may be extracted.

The convolution layer obtains a feature map by taking a non-linear activation function from the inner product of the filter and the local receptive field with respect to each patch of an input image. Compared with another network structure, the CNN has a feature using a filter having sparse connectivity and shared weights. Such a connection structure reduces the number of parameters to learn and makes learning through the backpropagation algorithm efficient, and the prediction performance is consequently improved.

The pooling layer or the sub-sampling layer generates a new feature map using area information of the feature map obtained by the previous convolution layer. In general, the feature map newly generated by the pooling layer decreases to a size smaller than an original feature map. There are max pooling for selecting a maximum value in a corresponding area in the feature map and average pooling for obtaining an average value in the corresponding area in the feature map as representative pooling methods. In general, the feature map in the pooling layer may be less influenced by a location of any structure or pattern which is present in an input image than a feature map in a previous layer. In other words, the pooling layer may extract a feature which is more robust to a regional change, such as noise or distortion in an input image or a previous feature map. Such a feature may play an important role in classification performance. An another role of the pooling layer is to reflect the characteristics of a wider area as going up to the higher learning layer in the deep structure, which may be to generate a feature which reflects a regional feature in a lower layer and reflects a more abstract feature of the entire image as higher layers go up, as feature extraction layers are stacked.

As described above, as a classification model such as multi-layer perception (MLP) or support vector machine (SVM) is combined in the form of a fully-connected layer, the feature finally extracted through repetition of the convolution layer and the pooling layer may be used to train and predict the classification model.

However, the structure of the DNN according to embodiments of the present disclosure is not limited thereto. The DNN according to embodiments of the present disclosure may be formed as neural networks of various structures.

As an embodiment, in an operation of generating the image prediction model for diagnosis, the computing device 10 may input dynamic image data to the DNN in various manners to generate an image prediction model for diagnosis.

As an example, the computing device 10 may match and learn a change in each pixel of dynamic image data over time with each pixel in early image data and delay image data (e.g., a method using a recurrent neural network (RNN)).

Furthermore, as another example, the computing device 10 may learn delay image data by using each image frame in dynamic image data over time as a multi-channel input (e.g., a multi-channel convolutional neural network (CNN) method).

The processor 100 may obtain early dynamic image data including a playback interval image from a drug injection time point corresponding to dynamic image data for training to the first time and delay image data including a playback interval image after the reference time point.

In addition, the processor 100 may obtain blood flow image information based on the early dynamic image data and may obtain disease-specific information based on the delay image data. In detail, the processor 100 may obtain an image for flow of the drug by means of the early dynamic image data to obtain blood flow image information FOR a blood vessel structure or the like of the object.

On the other hand, because the drug is bound to a specific target area by means of the delay image data, the processor 100 may obtain disease-specific information associated with the state of the object depending on the bound target.

In detail, when FP-CIT is bound to a dopamine neurotransmitter which is a target portion, the processor 100 may determine that the object has Parkinson's disease. The processor 100 may form a first training dataset based on such an operation.

Furthermore, the processor 100 may predict new early dynamic image data and new delay image data corresponding to the dynamic image data for diagnosis based on the dynamic image data for diagnosis and the first training data.

In other words, the early dynamic image data and the delay image data corresponding to the dynamic image data for training may be mapped and learned to the first training data. Thereafter, when dynamic image data for diagnosis is input, the processor 100 may predict early dynamic image data and delay image data corresponding to the dynamic image data.

Furthermore, the processor 100 may normalize image data for training and image data for diagnosis based on a maximum value or an average value between brightness of the dynamic image data for training and brightness of the dynamic image data for diagnosis and may predict new early dynamic image data and new delay image data corresponding to the image data for diagnosis.

In other words, the forming of the first training data may be to match and learn a change in each pixel in the dynamic image data for training over time with each pixel in the early dynamic image data and the delay image data.

Meanwhile, it is obvious that the image data used by the processor 100 is able to be provided as positron emission tomography image data, but is able to be applied to the entire image associated with the medical field.

In other words, according to an embodiment of the present disclosure, the processor 100 may normalize brightness of dynamic image data on the basis of the maximum value or the average value to generate image data.

According to an embodiment of the present disclosure, when the drug used to capture image data is a tracer (e.g., Fluorodeoxyglucose (FDG) PET) in which the amount bound to the target area continues to increase over time, because a brightness ratio between a reference area and a target are varies with the drug dose because of the nature of the PET tracer which is ingested in proportion to the drug dose, the computing device 10 may perform normalization on the basis of the maximum value or the average value of the brightness of the dynamic image data to generate image data.

Meanwhile, the operation is described using the PET in the present disclosure, but the above-mentioned operation may be applied to MR as well as the PET and may be applied the overall medical imaging.

However, for the MR, the processor 100 may derive disease-specific information by means of the early dynamic image data and may derive blood flow image information by means of the delay image data.

When the drug used to capture image data is a tracker bound to a specific target area (when FP-CIT is used as the tracer), because parameters of a tracer model are the same as each other although the input and the output simultaneously and linearly increase and decrease in a linear tracer kinetic model which uses the reference area as the input and uses the target area as the output, the computing device 10 may normalize brightness of early dynamic image data for training and brightness of early dynamic image data for diagnosis on the basis of a maximum value or an average value to generate new delay image data.

In other words, when the drug used to capture the image data is the tracer bound to the specific target area, dynamic image data for training may be formed as image data obtained before a time point when the influence of blood flow is excluded from a time point when a dose ratio difference value between the target area and the reference area is greater than or equal to a specific value or the ratio difference value is maximized.

Furthermore, the dynamic image data for training may be formed as image data which is continuously or discontinuously obtained from a time point when the dose ratio difference value between the target area and the reference area is greater than or equal to the specific value or the amount of change in dose in the reference area due to flood flow decreases to a time point when the dose ratio difference between the target area and the reference area is maximized.

The dose ratio value may refer to a ratio between a radiation dose at an early time point and a radiation dose at a specific measurement time point.

Thus, the dose ratio difference value may refer to a difference value between a dose ratio of the target area and a dose ratio of the reference area.

In detail, the processor 100 may obtain information about doses of a target image and a reference image.

Furthermore, the processor 100 may obtain the dose corresponding to the target image and the dose corresponding to the reference image, may calculate ratio values of the respective doses, and may calculate a difference value between the respective dose ratios.

Furthermore, the processor 100 may determine a time point when the amount of change in dose in the reference area decreases and a time point when the dose ratio difference is maximized.

In general, when medical staff perform a diagnosis based on delay image data, they administer large amounts of drugs at an early time point to perform a diagnosis using delay image data captured with a sufficient radiation dose even after the radioactive isotope decreases due to physical half-life and excretion outside the body such as urination/defecation (i.e., physiological decrease). At this time, there is a problem in which the radiation dose provided to the patient's body increases.

Thus, by using the embodiment of the present disclosure, the computing device 10 may insert only a tracer sufficient to obtain a sufficient radiation dose to obtain dynamic image data for diagnosis and may insert the dynamic image data for diagnosis into the prediction model to obtain early dynamic image data and final delay image data for diagnosis, thus reducing the amount of radioactive material injected into the patient to reduce a radiation dose provided to the body of the patient.

The predetermined reference time may be determined based on a type of the tracer.

Meanwhile, the processor 100 may form second training data for predicting blood flow image information and disease-specific information from the early dynamic image data and the delay image data based on a second image prediction model for diagnosis, which uses the early dynamic image data and the delay image data.

To sum up, the first prediction model for diagnosis may predict the early dynamic image data and the delay image data from the dynamic image data and may learn and predict the blood flow image information and the disease-specific information corresponding to them, whereas the second prediction model for diagnosis may perform learning based on the early dynamic image data and the delay image data corresponding to the dynamic image data and may predict blood flow image information and disease-specific information in an integrated manner, when early dynamic image data for diagnosis or delay image data is input later.

Meanwhile, the processor 100 may determine a state of the object based on the blood flow image information and the disease-specific information.

In detail, the processor 100 may derive information about whether the object has Parkinson's disease or dementia using the disease-specific information and the blood flow image information of the object, which are derived in the above-mentioned method.

In detail, when the tracer remains in the dopamine neurotransmitter of the object, the processor 100 may determine that the object has Parkinson's disease.

Furthermore, when amyloid tracer remains, the processor 100 may determine that the object has dementia.

The processor 100 may determine an image prediction model for diagnosis, which has higher accuracy between the accuracy of the first image prediction model for diagnosis and the accuracy of the second image prediction model for diagnosis.

For example, when a diagnoser performs a diagnosis using early dynamic image data, the processor 100 may calculate accuracy of the first prediction model for diagnosis with respect to Parkinson's disease and accuracy of the second prediction model for diagnosis with respect to Parkinson's disease. In this case, the processor 100 may select a prediction model for diagnosis, which has higher accuracy, among respective prediction models for diagnosis and may determine a state of the object.

A detailed description associated with it will be described below.

At least one component is added or deleted in response to performance of the components of the computing device 10 shown in FIG. 1. Furthermore, it may be easily understood to those skilled in the art that mutual positions of the components are able to change in response to the performance or structure of the system.

Meanwhile, each component shown in FIG. 1 refers to software and/or a hardware component such as a field programmable gate array (FPGA) and an application specific integrated circuit (ASIC).

Figure 2:
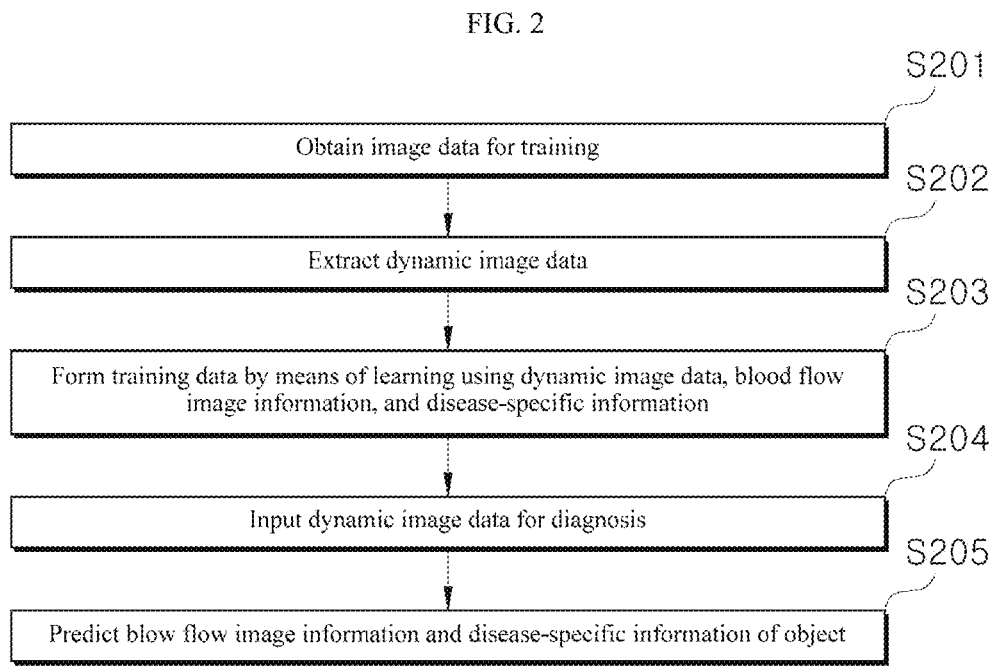
FIG. 2 is a flowchart for describing an operation of predicting blood flow image information and disease-specific information of an object using dynamic image data according to an embodiment of the present disclosure.

FIG. 2 is a flowchart for describing an operation of predicting blood flow image information and disease-specific information of an object using dynamic image data according to an embodiment of the present disclosure.

Referring to FIG. 2, in operation S201, a computing device may obtain image data for training. As described above, the image data for training may include all of pieces of image data at a time point when delay image data is obtained from a time point after a tracer or a contrast agent is administered to an object.

In operation S202, the computing device may extract dynamic image data from the image data for training.

The dynamic image data for training may refer to image data in which early dynamic image data and delay image data are excluded from the image data for training.

Thereafter, in operation S203, the computing device may match and learn the dynamic image data for training with blood flow image information and disease-specific information to form training data. A detailed operation for generating the training data will be described below.

Meanwhile, when dynamic data for diagnosis for diagnosing the object is then input in operation S204, in operation S205, the computing device may predict blood flow image information and disease-specific information corresponding to the dynamic data for diagnosis.

Figure 3:
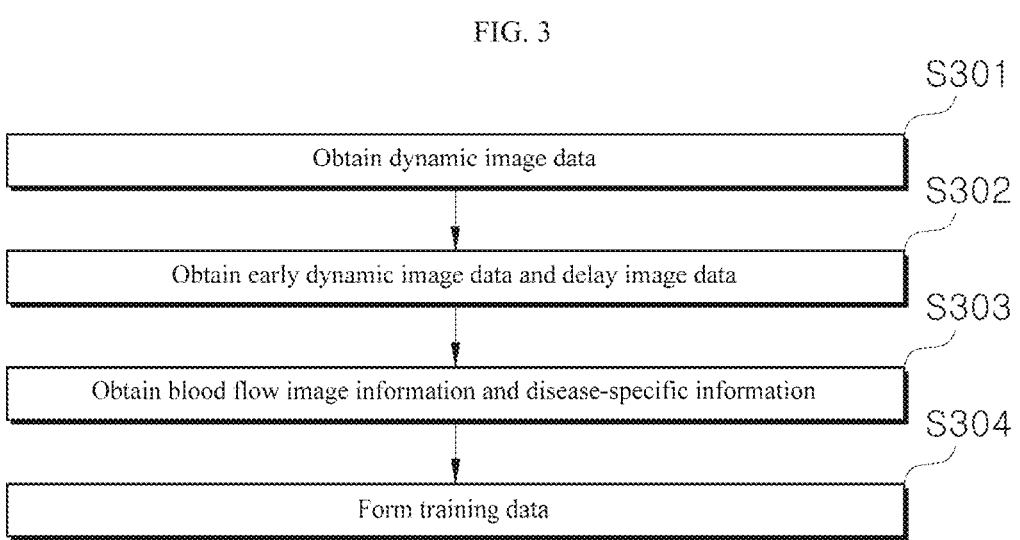
FIG. 3 is a drawing for describing an operation of generating training data in a prediction model for diagnosis according to an embodiment of the present disclosure.

FIG. 3 is a drawing for describing an operation of generating training data in a prediction model for diagnosis according to an embodiment of the present disclosure.

FIG. 3 is a flowchart illustrating an operation of forming training data in FIG. 2.

Referring to FIG. 3, in operation S301, a computing device may obtain dynamic data for training.

The dynamic image data for training may be formed by excluding early dynamic image data and delay image data from image data for training.

Meanwhile, in operation S302, the computing device may obtain the early dynamic image data and the delay image data together in obtaining the dynamic image data.

In operation S303, the computing device may obtain blood flow image information from the early dynamic image data and may obtain disease-specific information from the delay image data.

In other words, in operation S304, the computing device may match and learn the dynamic image data with the early dynamic image data and the delay image data and may additionally combine the blood flow image information matched with the early dynamic image data and the disease-specific information matched with the delay image data information to generate training data.

The computing device according to an embodiment may use the early dynamic image data, the dynamic image data, and the delay image data in generating such training data and may perform learning using a dataset which uses results of reading Parkinson's disease and atypical Parkinson's disease when the object is normal and abnormal or when the object is normal, when the object is a brain.

Figure 4:
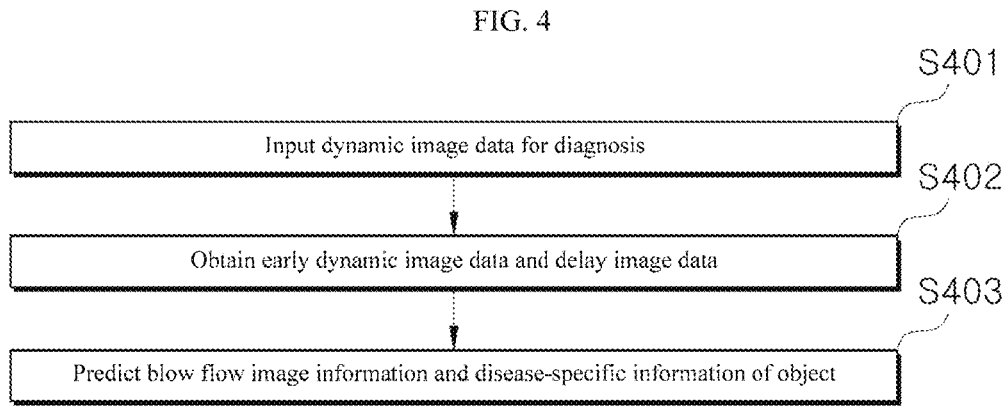
FIG. 4 is a flowchart for describing an operation of predicting blood flow image information and disease-specific information of an object based on dynamic image data for diagnosis according to an embodiment of the present disclosure.

FIG. 4 is a flowchart for describing an operation of predicting blood flow image information and disease-specific information of an object based on dynamic image data for diagnosis according to an embodiment of the present disclosure.

In other words, FIG. 4 illustrates a subsequent operation when dynamic data for diagnosis is input after training data is generated.

In detail, referring to FIG. 4, when dynamic image data for diagnosis is input after training data is generated in operation S401, in operation S402, a computing device may predict early dynamic image data and delay image data based on dynamic image data using primarily and previously formed training data.

Thereafter, in operation S403, the computing device may predict blood flow image information and disease-specific information of an object, which correspond to each image data.

Figure 5:
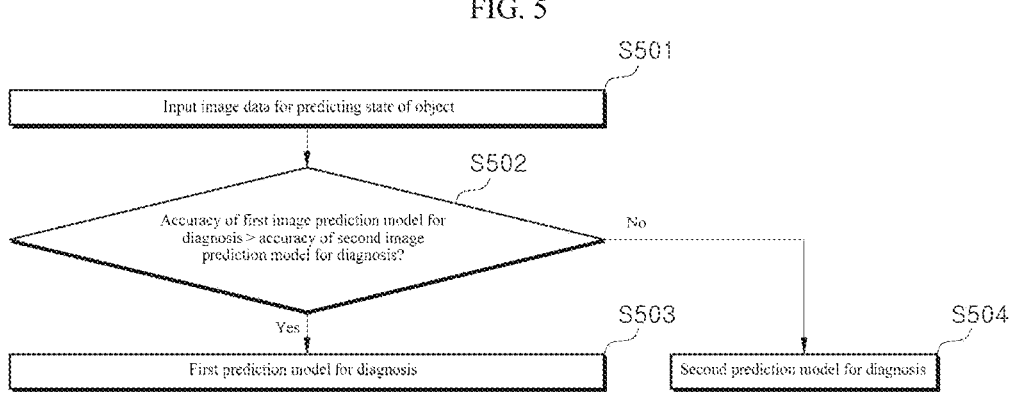
FIG. 5 is a flowchart for describing an operation of comparing accuracy of a first prediction model for diagnosis with accuracy of a second prediction model for diagnosis to predict a state of an object according to an embodiment of the present disclosure.

FIG. 5 is a flowchart for describing an operation of comparing accuracy of a first prediction model for diagnosis with accuracy of a second prediction model for diagnosis to predict a state of an object according to an embodiment of the present disclosure.

A computing device may use a first prediction model for diagnosis and a second prediction model for diagnosis to predict a state of an object.

The first prediction model for diagnosis may refer to a model for predicting early dynamic image data and delay image data based on dynamic image data and predicting a state of the object based on them.

The second prediction model for diagnosis may refer to a model for predicting blood flow image information and disease-specific information of the object based on the early dynamic image data and the delay image data.

In operation S501, the computing device may input image data for predicting a specific state. According to an embodiment, the computing device may input image data for diagnosing Parkinson's disease.

In this case, when the accuracy of the first prediction model for diagnosis is greater than the accuracy of the second prediction model for diagnosis, in operations S502 and S503, the computing device may predict a state of the object using the first prediction model for diagnosis. Meanwhile, when the accuracy of the second prediction model for diagnosis is greater than the accuracy of the first prediction model for diagnosis, in operations S502 and S503, the computing device may predict the state of the object using the first prediction model for diagnosis.

However, in this case, when the accuracy of the second prediction model for diagnosis is greater than the accuracy of the first prediction model for diagnosis, in operation S504, the computing device may predict the state of the object using the second prediction model for diagnosis.

Meanwhile, the operation of the present disclosure, which is described with reference to FIGS. 2 to 5, is merely an embodiment of the present disclosure. There is no limit in the operation of forming the training data and receiving the diagnosis image data and predicting the state of the object.

Figure 6:
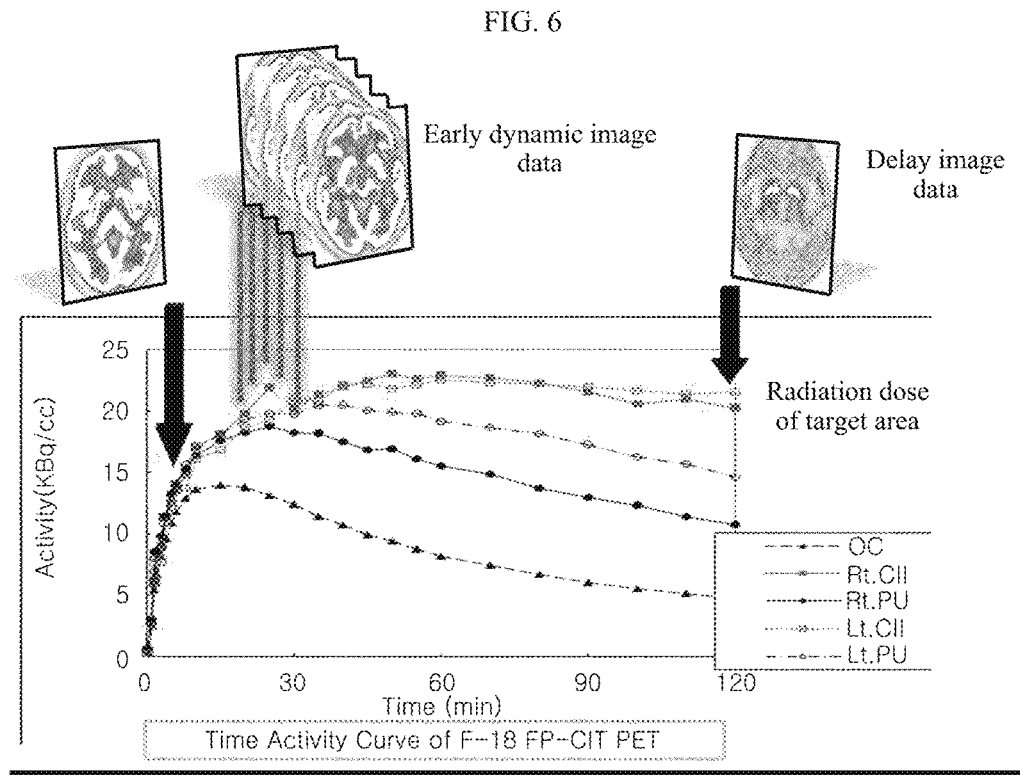
FIG. 6 is a drawing for describing early dynamic image data, dynamic image data, and delay image data according to an embodiment of the present disclosure.

FIG. 6 is a drawing for describing early dynamic image data, dynamic image data, and delay image data according to an embodiment of the present disclosure.

Referring to FIG. 6, when FP-CIT is used as a drug (i.e., a tracer), it is difficult to perform a diagnosis because the radiation dose appears high in the entire area of the brain due to the influence of blood flow in an early time range in which the drug is administered. However, as the drug is metabolized and excreted through urine or liver and its concentration in plasma decreases as time passes, because the drug disappears from the blood, the drug drains from brain tissue into the blood to balance things out. A computing system obtains early dynamic image data in a first time range in which the radiation dose in the brain tissue changes.

Thereafter, because FP-CIT has a strong binding force with dopamine and is therefore effective in diagnosing Parkinson's disease, as it is bound to the dopamine neurotransmitter which is a target portion, even if the blood flow effect in other areas decreases over time and the concentration decreases, the target portion maintains a high concentration. Thus, the computing system obtains delay image data at a time point when a reference time elapses after the drug is administered and the influence of blood flow decreases. The delay image data may be image data used to previously diagnose a size, a shape, or the like of the target portion by medical staff.

Herein, corresponding image data between early dynamic image data and delay image data may correspond to dynamic image data.

Furthermore, as another embodiment, when the drug used to capture image data is a tracer bound to a specific target area, a first time range in which the early dynamic image data is obtained may be determined based on various criteria. For example, the first time range may be set to a time range after a time point when influence by blood flow starts to decrease in a reference area The reference area may be a specific portion of the brain in which there is no material to which the tracer is bound or there is no difference between diseases because the material is small. The reference area may vary with a type and a characteristic of the tracer. For example, when the tracer is FP-CIT, the reference area is a portion in which a dopamine neurotransmitter, such as cerebellum or occipital cortex, is low. Furthermore, as another example, the first time range may be set around a time point when a dose ratio difference value between the target area and the reference area is greater than or equal to a specific value or the ratio difference value is maximized.

As another embodiment, when the drug used to capture image data is a tracer (e.g., Fluorodeoxyglucose (FDG) PET) in which the amount bound to the target area continues increasing over time, because the dose increases in each area of the brain without a peak point, the computing system obtains early dynamic image data in the early first time range in which the difference in radiation dose is not large and obtains delay image data at a reference time point when a radiation dose difference ratio between areas increases.

In this case, image data between early dynamic image data and delay image data may also correspond to dynamic image data.

Figure 7A:
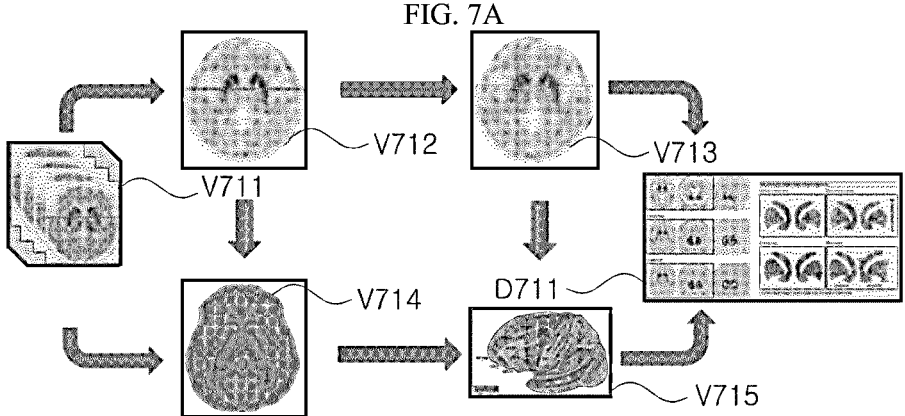
FIGS. 7A and 7B are drawings for describing a relationship among dynamic image data, early dynamic image data, and delay image data according to an embodiment of the present disclosure.
Figure 7B:
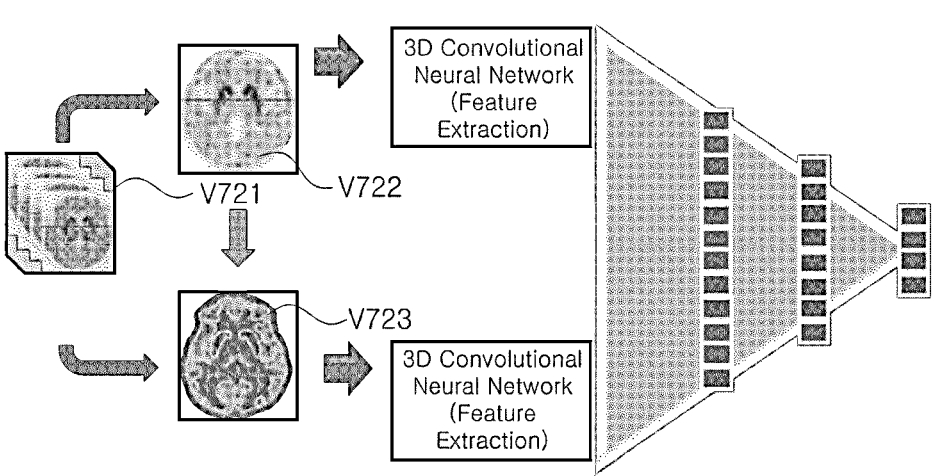

FIGS. 7A and 7B are drawings for describing a relationship among dynamic image data, early dynamic image data, and delay image data according to an embodiment of the present disclosure.

Meanwhile, FIG. 7A illustrates a drawing for describing an operation based on a first prediction model for diagnosis in the present disclosure. FIG. 7B illustrates a drawing for describing an operation based on a second prediction model for diagnosis in the present disclosure.

Referring to FIG. 7A, a computing device may obtain dynamic image data (V711).

Thereafter, the computing device may predict early dynamic image data V714 and delay image data V712 using the above-mentioned first training data.

The computing device may set a region of interest of delay image data through an operation of setting a striatum region of interest based on deep learning (V713).

Thereafter, the computing device may predict disease-specific information by means of quantification for each detailed area specialized for a delayed image.

According to an embodiment of the present disclosure, the computing device may perform prediction by means of quantification of the dopamine transporter in the striatum.

Meanwhile, the computing device may predict early dynamic image data based on dynamic image data (V714). Thereafter, the computing device may set a region of interest based on deep learning.

Thereafter, the computing device may perform quantification for each area of quantification brain cortex for each detailed area specialized for early dynamic image data.

Meanwhile, FIG. 7B is a drawing illustrating an operation of the present disclosure using a second prediction model for diagnosis.

Referring to FIG. 7B, the computing device may predict delay image data V722 and early dynamic image data V723 based on dynamic image data V721 and may perform a diagnosis of an object by means of dopamine or blood flow information fusion based on deep learning.

Meanwhile, the blood flow image information and the disease-specific information described with reference to FIGS. 7A and 7B are merely an embodiment for describing an operation of the present disclosure. There is no limit in information included in anatomy information and the disease-specific information.

Figure 8A:
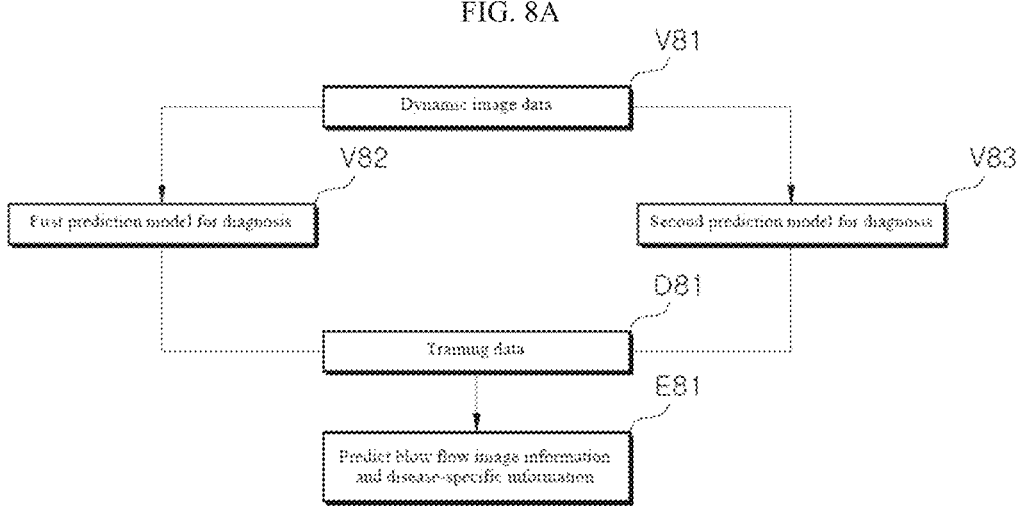
FIGS. 8A, 8B, and 8C are drawings for describing an operation of predicting a state of an object using both of a first prediction model for diagnosis and a second prediction model for diagnosis according to an embodiment of the present disclosure.
Figure 8B:
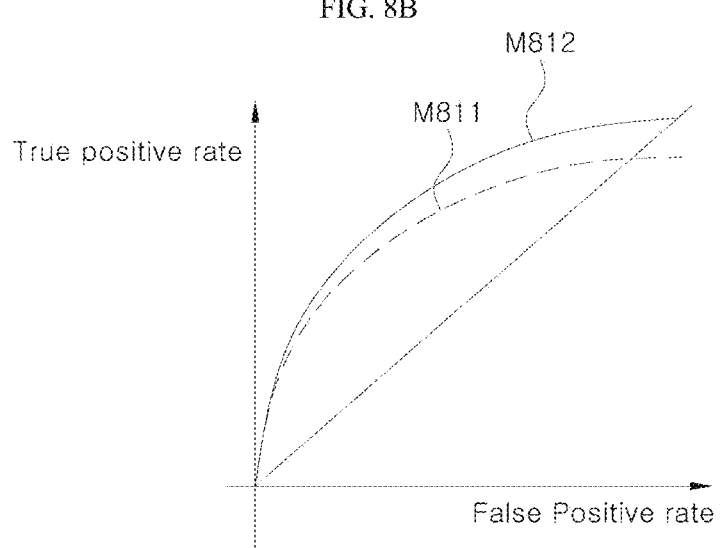
Figure 8C:
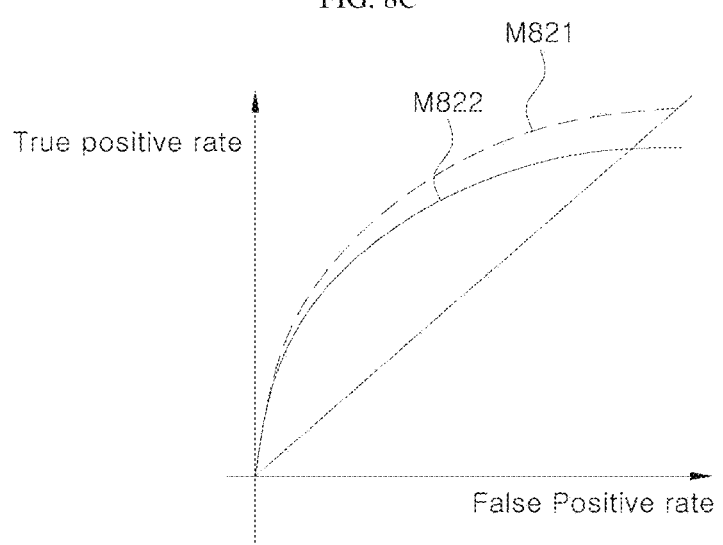

FIGS. 8A, 8B, and 8C are drawings for describing an operation of predicting a state of an object using both of a first prediction model for diagnosis and a second prediction model for diagnosis according to an embodiment of the present disclosure.

Referring to FIGS. 8A, 8B, and 8C, in predicting a state of an object from image data, a computing device may predict the state using ensemble algorithms of a first prediction model for diagnosis and a second prediction model for diagnosis.

The ensemble learning may refer to a technique for generating several classifiers and combining the predictions to derive a more accurate prediction. The computing device may combine several weak models to predict a more accurate prediction, rather than using one strong model.

Referring to FIGS. 8A and 8B, the first prediction model for diagnosis and the second prediction model for diagnosis for predicting blood flow image information and disease-specific information of the object based on the above-mentioned operation are illustrated.

The first prediction model (V82) for diagnosis may refer to a prediction model for diagnosis for predicting early dynamic image data and delay image data based on dynamic image data (V81) obtained by the computing device and learning blood flow image information and disease-specific information based on them.

The second prediction model (V83) for diagnosis may form second training data based on the above-mentioned operation and may predict blood flow image information and disease-specific information, when early dynamic image data or delay image data of a diagnosis object is then input (E81).

Meanwhile, the computing device may determine accuracy of each prediction model for diagnosis at a time point of image data. An ROC curve may be used to determine such accuracy.

Furthermore, an artificial neural network after a 3D CNN of FIG. 8A may include a process of fusing features by means of a fully-connected layer.

Referring to FIGS. 8B and 8C, an ROC curve of the accuracy of predicting a blood flow image feature from an early time point of image data, that is, from the beginning to a first time is illustrated.

The ROC curve may be a measure to evaluate the accuracy of a prediction model for diagnosis. The Y-axis may refer to a true positive rate and the X-axis may refer to a false positive rate. When the ROC curve has a wide area, the prediction model for diagnosis may be evaluated as a prediction model for diagnosis, which has high accuracy.

FIG. 8B illustrates that an ROC curve M812 of the second prediction model for diagnosis is greater in area than an ROC curve M811 of the first prediction model for diagnosis.

Herein, the area of each curve may refer to an area below, that is, an area under the curve (AUC).

In this case, because it is shown that the accuracy of the model in an area from an early time point of image data to a first time point is higher in the second prediction model for diagnosis, the computing device may diagnose a state of an object using the second prediction model for diagnosis.

Meanwhile, referring to FIG. 8C, FIG. 8C illustrates an ROC curve corresponding to the accuracy of predicting disease-specific information based on dynamic image data before a reference time from a first time of image data.

In this case, because an ROC curve M821 corresponding to the first prediction model for diagnosis is greater in area than an ROC curve M822 corresponding to the second prediction model for diagnosis, the computing device may determine that the accuracy of the first prediction model for diagnosis is higher than the accuracy of the second prediction model for diagnosis in the corresponding area. Thus, in this case, the computing device may predict information of the object using the first prediction model for diagnosis.

Based on the above-mentioned method, the computing device may perform learning using the prediction model for diagnosis, which has higher accuracy, depending on a time point of the image data.

The method for predicting the state of the object based on the dynamic image data and the computing device for performing the same according to an embodiment of the present disclosure may perform learning based on dynamic image data captured at a time point when both of blood flow image information and disease-specific information are included to predict early dynamic image data and delay image data and may additionally provide the blood flow image information and the disease-specific information of the object.

The method for predicting the state of the object based on the dynamic image data and the computing device for performing the same according to an embodiment of the present disclosure may use dynamic image data including a large amount of information, thus improving the accuracy of diagnosis.

The method for predicting the state of the object based on the dynamic image data and the computing device for performing the same according to an embodiment of the present disclosure may provide a diagnosis prediction model with improved accuracy by using a prediction model for diagnosis for performing a diagnosis based on previous early image data and delay image data and a prediction model for diagnosis based on dynamic image data.

The method for predicting the state of the object based on the dynamic image data and the computing device for performing the same according to an embodiment of the present disclosure may use a smaller amount of drug when obtaining early dynamic image data for diagnosis than when injecting the drug to directly obtain delay image data, thus reducing a radiation dose which affects the body of the patient or reducing an image acquisition time, while obtaining the same quality of image.

The above-mentioned method for generating the image for diagnosis based on the early dynamic image data according to an embodiment of the present disclosure may be combined with a computer which is hardware and may be stored in a medium to be implemented as a program (or application) to be executed.

For the computer to read the program and execute the methods implemented with the program, the above-mentioned program may include a code coded into a computer language such as C, C++, Java, or a machine language readable through a device interface of the computer by a processor (CPU) of the computer. Such a code may include a functional code associated with a function and the like defining functions necessary for executing the methods and may include a control code associated with an execution procedure necessary for the processor of the computer to execute the functions according to a procedure. Further, such a code may further include a code associated with memory reference about whether additional information or media necessary for the processor of the computer to execute the functions is referred at any location (address number) of an internal or external memory of the computer. Further, if it is necessary for the processor of the computer to communicate with any computer or server located in a remote place to execute the functions, the code may further include a communication related code about how communication is performed with any computer or server located in a remote place using a communication module of the computer and whether to transmit and receive any information or media upon communication.

The medium may refer to a device-readable medium which stores data on a semipermanent basis rather than a medium, such as a register, a cache, or a memory, which stores data during a short moment. The medium may refer to a device-readable medium which stores data on a semipermanent basis rather than a medium, such as a register, a cache, or a memory, which stores data during a short moment. In other words, the program may be stored in various storage media on various servers accessible by the computer or various storage media on the computer of the user. Further, the medium may be distributed to a computer system connected over a network and may store a computer-readable code on a distributed basis.

While the present disclosure has been described with reference to exemplary embodiments, it will be apparent to those skilled in the art that various changes and modifications may be made without departing from the spirit and scope of the present disclosure. Therefore, the embodiments described above are provided by way of example in all aspects, and should be construed not to be restrictive.

What is claimed is:

1. A method for predicting a state of an object based on dynamic image data, the method being performed by an apparatus and comprising:

obtaining a plurality of pieces of image data for training;

extracting a plurality of pieces of dynamic image data for training from the plurality of pieces of image data for training, the plurality of pieces of dynamic image data for training including a playback interval image from a first time when a blood flow influence starts to decrease to a predetermined reference time point, after a time point when a drug is injected into a learning object included in each of the plurality of pieces of image data for training;

obtaining blood flow image information and disease-specific information corresponding to the plurality of pieces of dynamic image data for training;

performing learning using a first image prediction model for diagnosis to generate first training data, based on the blood flow image information and the disease-specific information corresponding to the plurality of pieces of dynamic image data for training; and predicting the blood flow image information and the disease-specific information corresponding to a diagnosis object using dynamic image data for diagnosis and the first training data, when the dynamic image data for diagnosis corresponding to the diagnosis object is obtained.

2. The method of claim 1, further comprising:

obtaining early dynamic image data including a playback interval image from the time point when the drug is injected to the first time, the early dynamic image data corresponding to the dynamic image data for training, and delay image data including a playback interval image after the reference time point, wherein the obtaining of the blood flow image information and the disease-specific information corresponding to the plurality of pieces of dynamic image data for training includes:

obtaining the blood flow image information based on the early dynamic image data and obtaining the disease-specific information based on the delay image data.

3. The method of claim 2, wherein the predicting of the blood flow image information and the disease-specific information corresponding to the diagnosis object includes:

predicting new early dynamic image data and new delay image data corresponding to the dynamic image data for diagnosis based on the dynamic image data for diagnosis and the first training data.

4. The method of claim 3, wherein the predicting of the blood flow image information and the disease-specific information corresponding to the dynamic image data for diagnosis includes:

normalizing the image data for training and image data for diagnosis based on a maximum value or an average value between brightness of the dynamic image data for training and brightness of the dynamic image data for diagnosis and predicting the new early dynamic image data and the new delay image data corresponding to the image data for diagnosis.

5. The method of claim 3, wherein the forming of the first training data includes:

matching and learning a change in each pixel in the dynamic image data for training over time with each pixel in the early dynamic image data and the delay image data.

6. The method of claim 1, wherein the image data for training is positron emission tomography image data.

7. The method of claim 1, wherein, when the drug used to capture the image data for training is a tracer bound to a specific target area, the dynamic image data for training is formed as image data obtained continuously or discontinuously from a time point when a dose ratio difference value between the target area and a reference area is greater than or equal to a specific value or an amount of change in dose in the reference area due to blood flow decreases to a time point when the dose ratio difference value is maximized.

8. The method of claim 7, wherein the predetermined reference time point is determined based on a type of the tracer.

9. The method of claim 2, further comprising:

predicting early dynamic image data and delay image data using the dynamic image data for training by means of a second image prediction model for diagnosis; and using the predicted early dynamic image data and the predicted delay image data together to form second training data for predicting the blood flow image information and the disease-specific information.

10. The method of claim 9, further comprising:

predicting the blood flow image information and the disease-specific information, using an image prediction model for diagnosis, the image prediction model having higher accuracy between accuracy of the first image prediction model for diagnosis and accuracy of the second image prediction model for diagnosis, the first image prediction model for diagnosis and the second image prediction model for diagnosis corresponding to the image data.

11. A computing device, comprising:

a display;

a memory storing an image prediction model for diagnosis; and at least one processor configured to communicate with the display and the memory, wherein the at least one processor is configured to:

obtain a plurality of pieces of image data for training;

extract a plurality of pieces of dynamic image data for training from the plurality of pieces of image data for training, the plurality of pieces of dynamic image data for training including a playback interval image from a first time when a blood flow influence starts to decrease to a predetermined reference time point, after a time point when a drug is injected into a learning object included in each of the plurality of pieces of image data for training;

obtain blood flow image information and disease-specific information corresponding to the plurality of pieces of dynamic image data for training;

perform learning using a first image prediction model for diagnosis to generate first training data, based on the blood flow image information and the disease-specific information corresponding to the plurality of pieces of dynamic image data for training; and predict the blood flow image information and the disease-specific information corresponding to a diagnosis object using dynamic image data for diagnosis and the first training data, when the dynamic image data for diagnosis corresponding to the diagnosis object is obtained.

12. The computing device of claim 11, wherein the at least one processor is configured to:

further obtain early dynamic image data including a playback interval image from the time point when the drug is injected to the first time, the early dynamic image data corresponding to the dynamic image data for training, and delay image data including a playback interval image after the reference time point; and obtain the blood flow image information based on the early dynamic image data and obtain the disease-specific information based on the delay image data, when obtaining the blood flow image information and the disease-specific information corresponding to the plurality of pieces of dynamic image data for training.

13. The computing device of claim 12, wherein the at least one processor is configured to:

predicting new early dynamic image data and new delay image data corresponding to the dynamic image data for diagnosis based on the dynamic image data for diagnosis and the first training data, when predicting the blood flow image information and the disease-specific information corresponding to the diagnosis object.

14. The computing device of claim 13, wherein the at least one processor is configured to:

normalize the image data for training and image data for diagnosis based on a maximum value or an average value between brightness of the dynamic image data for training and brightness of the dynamic image data for diagnosis and predict the new early dynamic image data and the new delay image data corresponding to the image data for diagnosis, when predicting the blood flow image information and the disease-specific information corresponding to the dynamic image data for diagnosis.

15. The computing device of claim 13, wherein the at least one processor is configured to:

match and learn a change in each pixel in the dynamic image data for training over time with each pixel in the early dynamic image data and the delay image data, when forming the first training data.

* * * * *